United States Patent [19]

Sakashita

[11] Patent Number: 5,370,659
[45] Date of Patent: Dec. 6, 1994

[54] GRASPING FORCERS FOR MEDICAL TREATMENT

[75] Inventor: Kiyotoshi Sakashita, Tokyo, Japan

[73] Assignee: Olympus Optical Co., Ltd., Tokyo, Japan

[21] Appl. No.: 43,182

[22] Filed: Apr. 6, 1993

[30] Foreign Application Priority Data

Apr. 9, 1992 [JP] Japan ............... 4-088633
Apr. 20, 1992 [JP] Japan ............... 4-099411
Mar. 9, 1993 [JP] Japan ............... 5-048245

[51] Int. Cl.⁵ ............................... A61B 17/28
[52] U.S. Cl. ............................... 606/205; 128/751
[58] Field of Search .......... 606/51, 52, 174, 83, 606/127, 128, 205–211; 128/751–755; 604/22

[56] References Cited

U.S. PATENT DOCUMENTS

| | | | |
|---|---|---|---|
| 2,790,437 | 4/1957 | Moore | 606/170 |
| 3,404,677 | 10/1968 | Springer | 606/174 |
| 4,122,856 | 10/1978 | Morsior et al. | 606/174 |
| 4,569,131 | 2/1986 | Falk et al. | 128/751 |
| 5,147,357 | 9/1992 | Rose et al. | 606/51 |
| 5,176,702 | 1/1993 | Bales et al. | 128/751 |
| 5,201,759 | 4/1993 | Ferzli | 128/751 |
| 5,211,655 | 5/1993 | Hasson | 128/751 |

FOREIGN PATENT DOCUMENTS

0313820A2 5/1989 European Pat. Off. .

*Primary Examiner*—Stephen C. Pellegrino
*Assistant Examiner*—William W. Lewis
*Attorney, Agent, or Firm*—Frishauf, Holtz, Goodman & Woodward

[57] ABSTRACT

A fixed operation handle is provided at the proximal end portion of a sheath and a movable operation handle is rotatably connected to the fixed operation handle. A coupling rod engages with the movable operation handle so as to freely move the rod back and forth. An operation shaft is threadably coupled to the coupling rod and a forceps is connected to the distal end of the operation shaft. At the areas of the coupling rod and fixed operation handle through which the coupling rod is inserted, first and second stopper units are provided for adjustably restricting an end-of-forward and end-of-backward movement of the coupling rod, thereby serving as a stopper for opening and closing the movable operation handle.

12 Claims, 13 Drawing Sheets

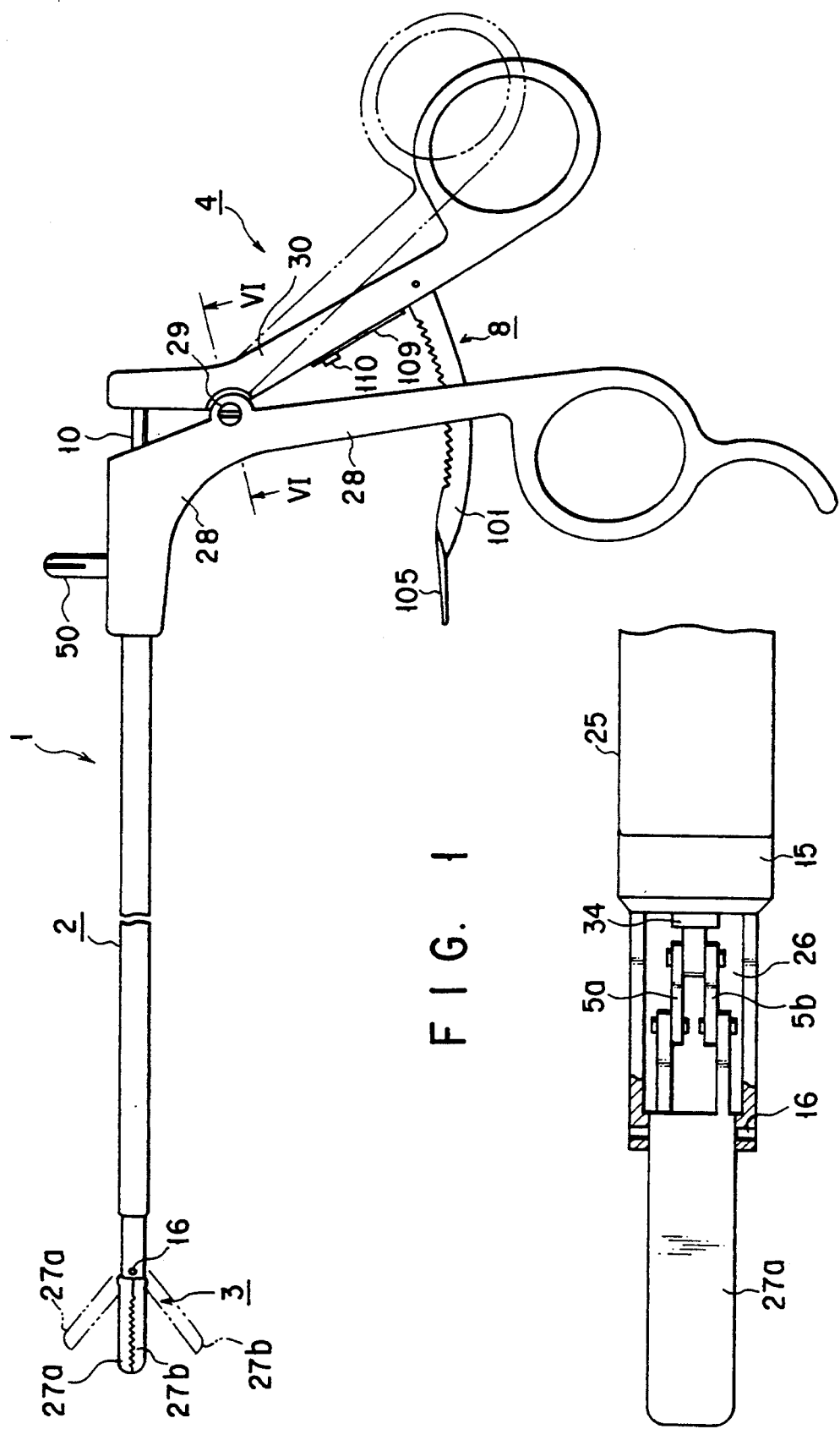

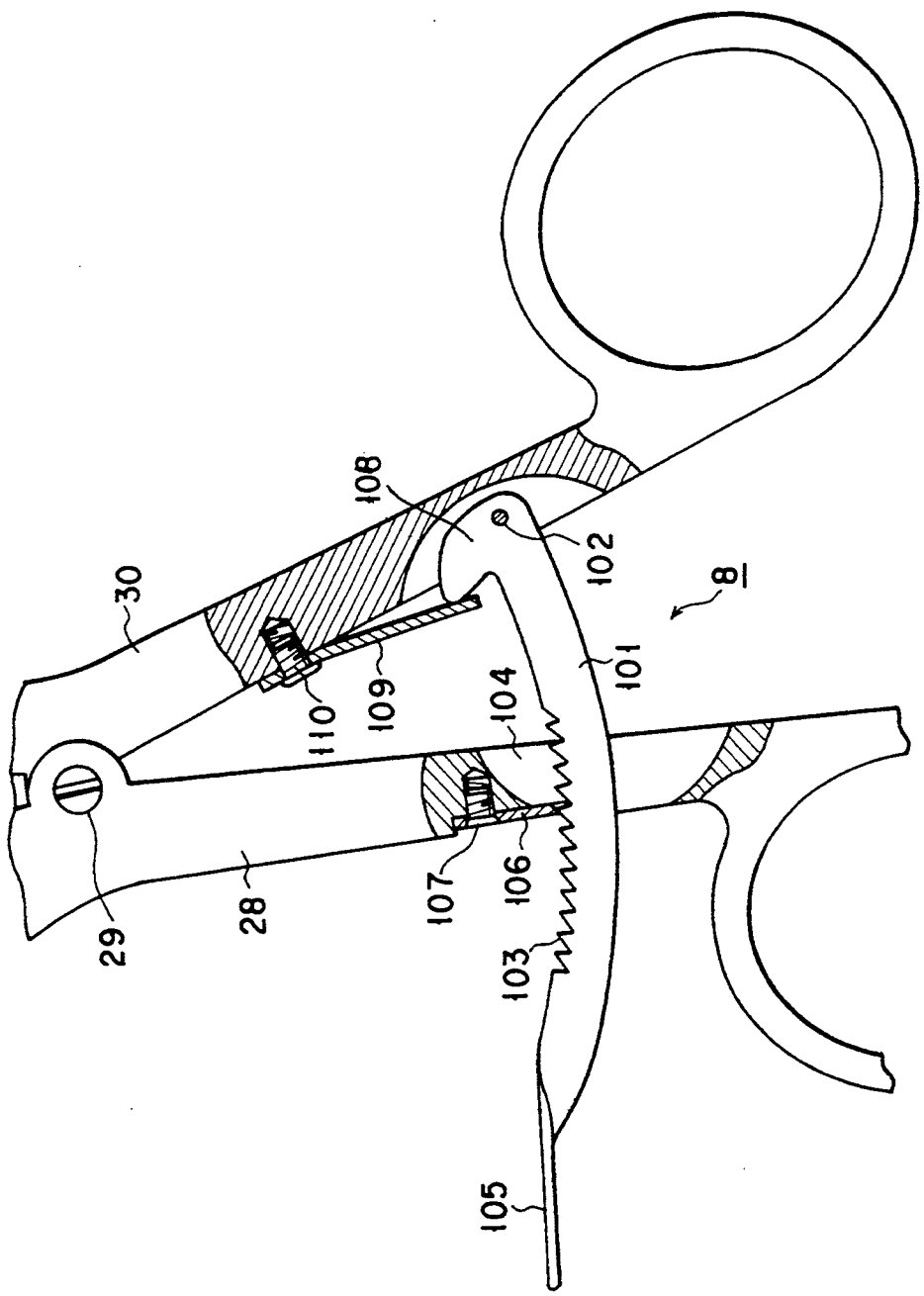
F I G. 7

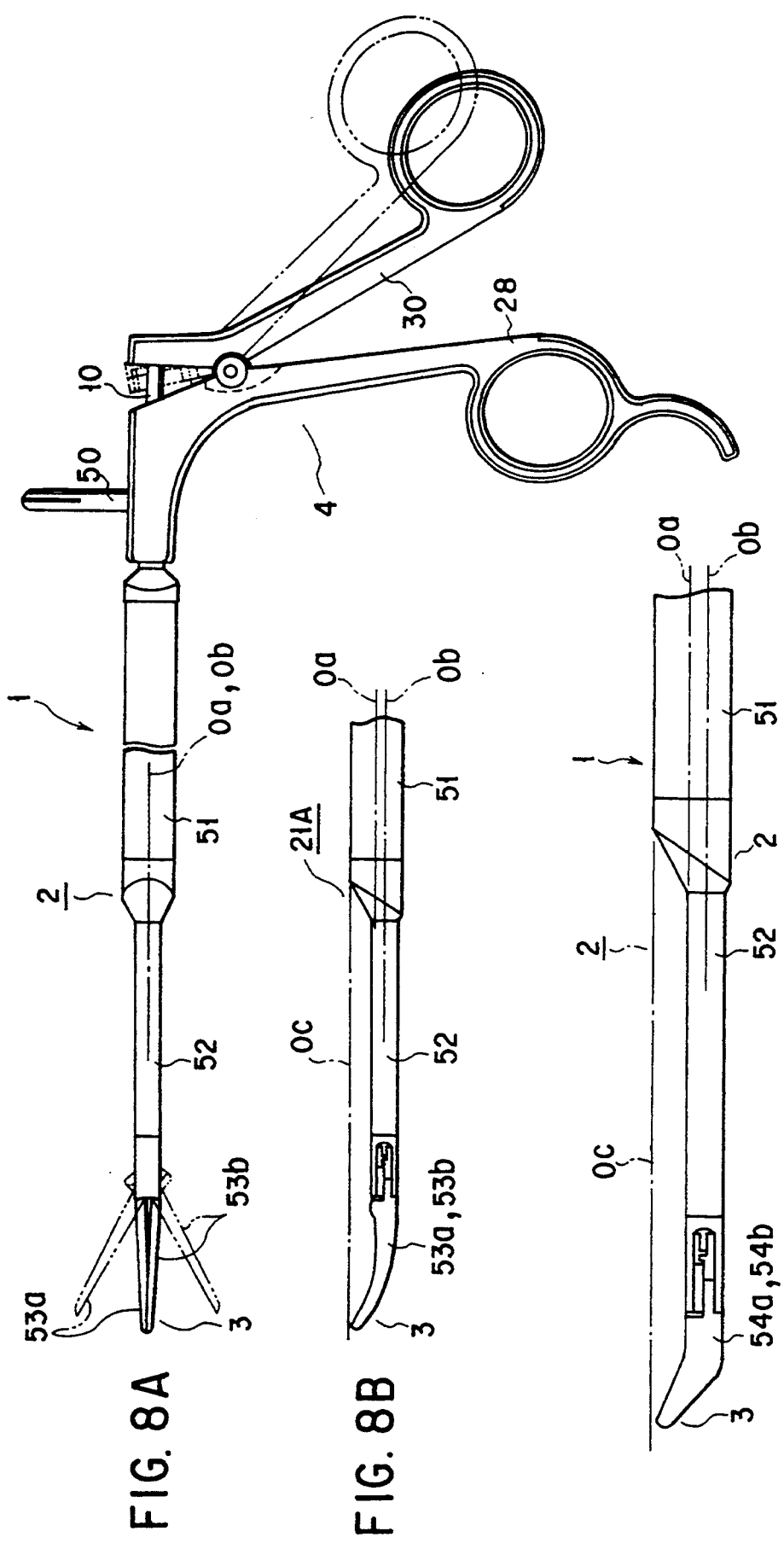

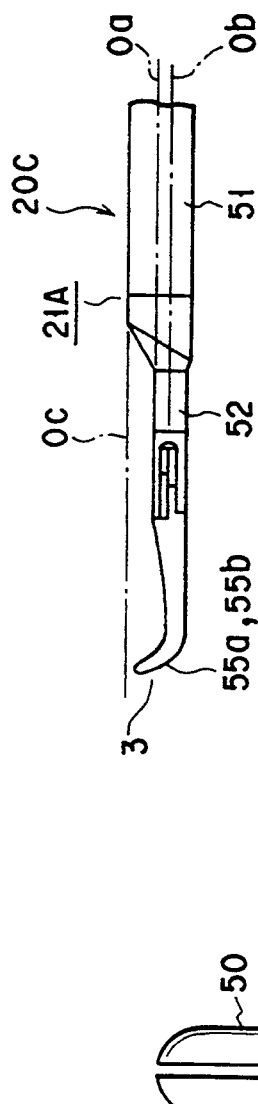
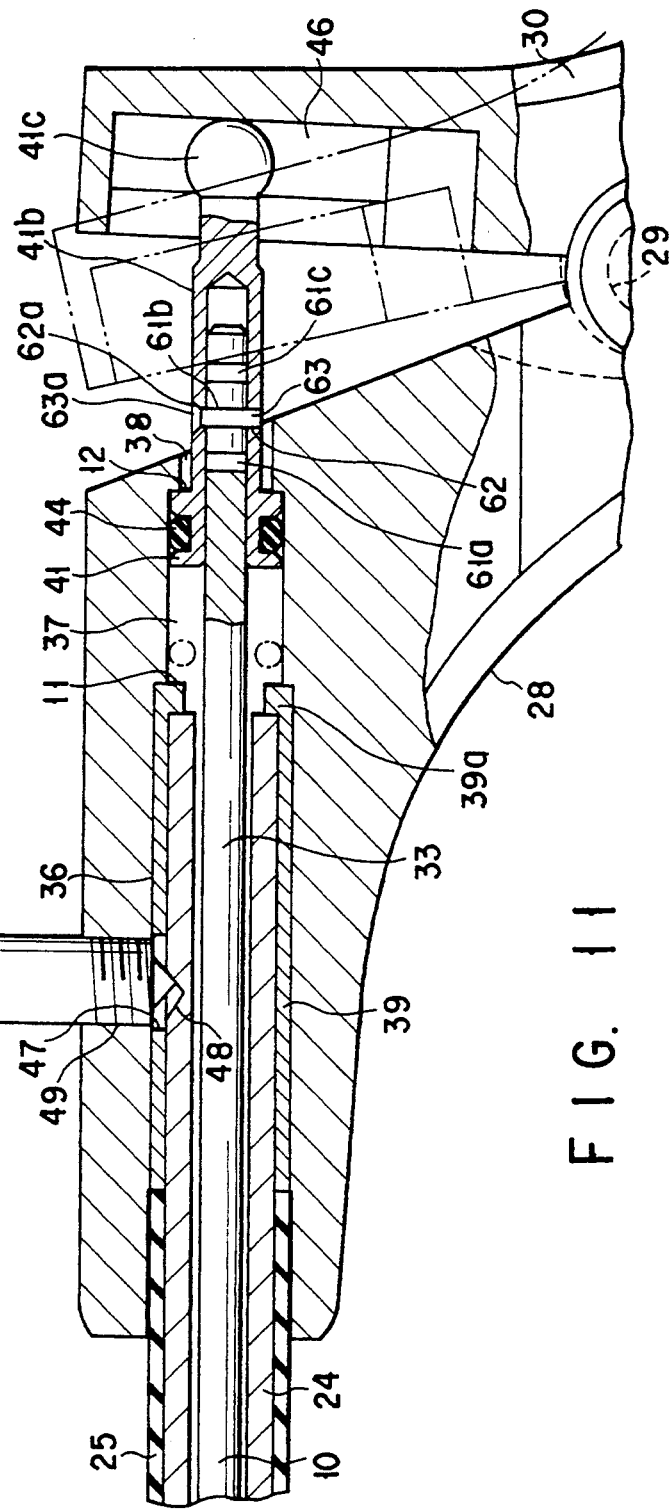
FIG. 10
FIG. 11

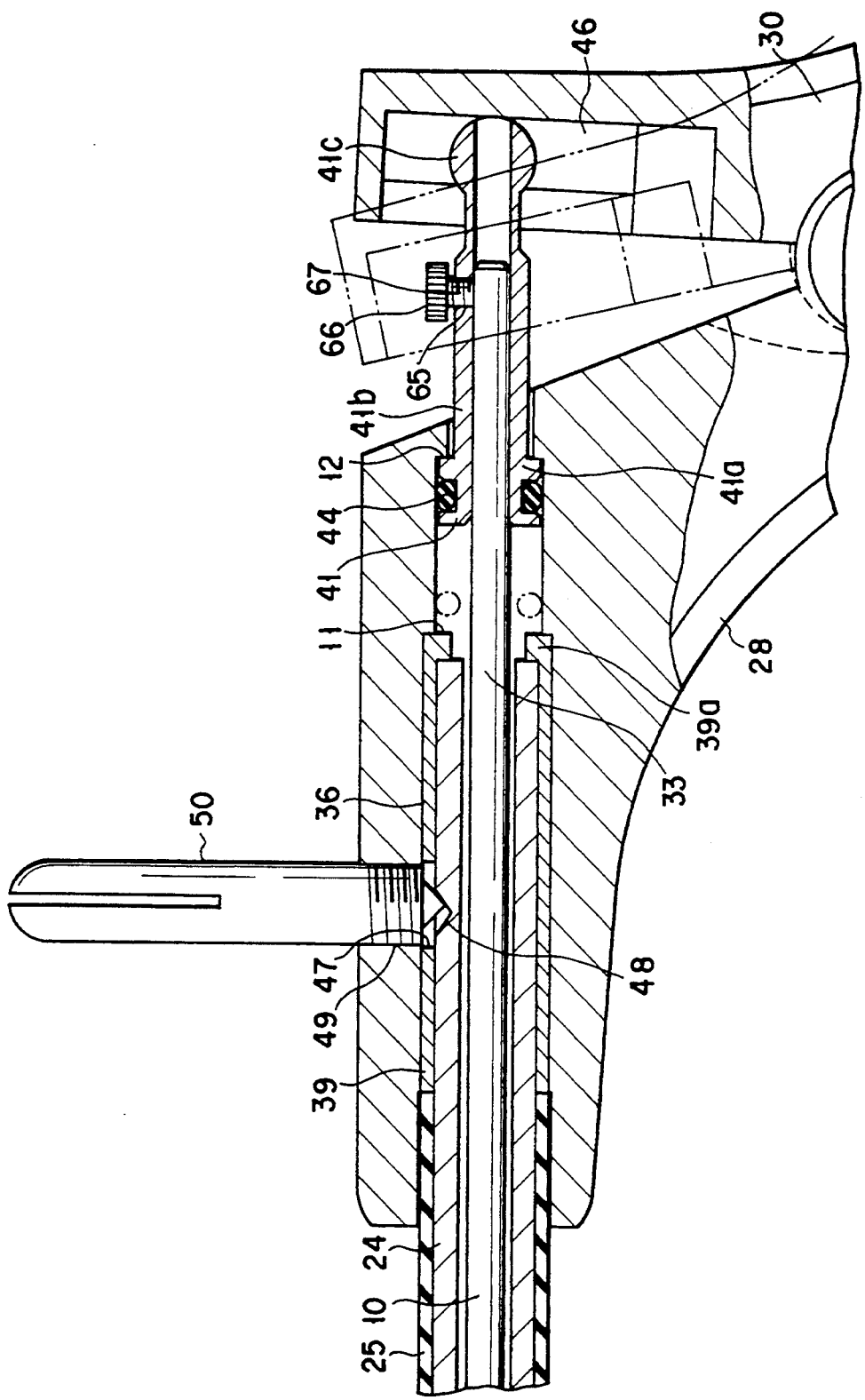

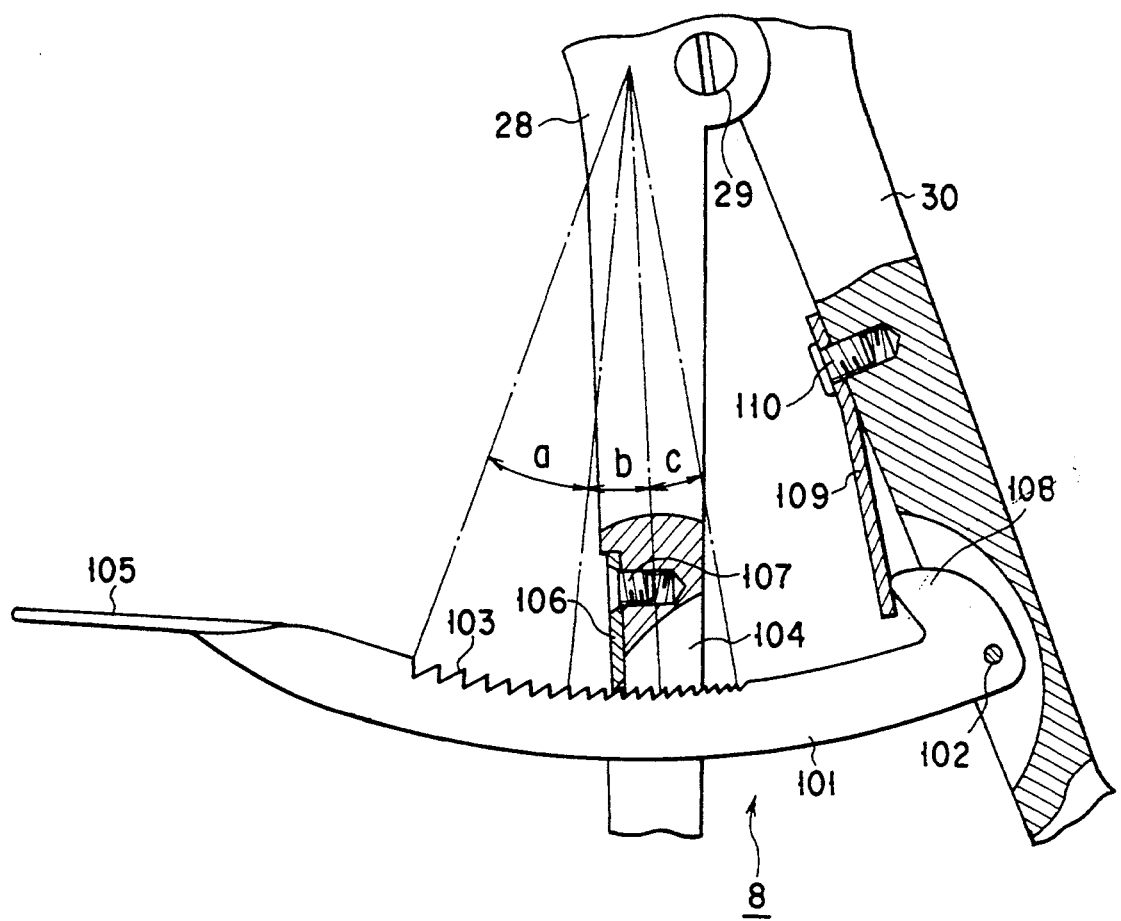
F I G. 18A
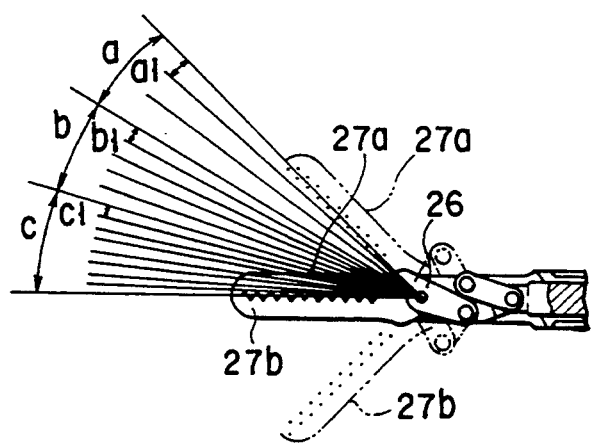
F I G. 18B

GRASPING FORCEPS FOR MEDICAL TREATMENT

BACKGROUND OF THE INVENTION

1. Field of the Invention

The present invention relates to grasping or gripping forceps for medical treatment which is used for gripping a living tissue, etc., of a subject, for example, in a laparoscopic surgery.

2. Description of the Related Art

Conventionally, a grasping or gripping forceps is known in, for example, Published Unexamined Japanese Patent Application 1-133907. In the forceps shown, a pair of gripping members are provided on the distal end of a sheath to be inserted into a body cavity of a subject through the cannula of a trocar/cannula device so as to allow these members to be opened and closed and an operation section is provided on a proximal end of the sheath so as to open and close the pair of gripping members. An operation shaft is inserted into the sheath so as to be movable back and forth. The distal end of the operation shaft is coupled to the gripping members through a link mechanism. The operation section comprises an operation handle fixed to the proximal end portion of the sheath and a movable operation handle swingable by a setscrew pin relative to the fixed operation handle.

The proximal end of the operation shaft is connected to the swinging operation end of the movable operation handle. When the movable operation handle is swung with the setscrew pin as a fulcrum, then the operation shaft is slidably moved back and forth to enable the pair of gripping members to be closed and opened through the link mechanism. By the remote operation at the operation section, the pair of gripping members are opened and closed to allow the living tissue in the body cavity, for example, an organ such as the gallbladder to be gripped thereby or released therefrom.

In this type of gripping forceps, care should be exercised not to tighten the distal gripping sections to an excessive extent by the swinging operation of the movable operation handle of the operation section. One countermeasure is to provide a stopper pin on that area of the fixed operation handle oppositely facing the movable operation handle so that, even when the movable operation handle is to be closed relative to the fixed operation handle to a more than necessary extent, the movable operation handle abuts against the projecting end of the stopper pin and is prevented from any further swinging movement.

In such conventional gripping forceps, the stopper pin, being projected from the area of the fixed operation handle, provides an obstacle from its operational point of view. Further, the stopper pin effectively acts as such when the distal gripping areas are closed, but serves no purpose when they are opened.

Further an amount of projection of the stopper pin is fixed and, therefore, the movable operation handle is stopped at all times to a given abutting position. In actual practice, however, various forms of living tissue have to be gripped as to-be-gripped objects and it is often of advantage to set the stopper position adjustable instead of setting it fixed.

SUMMARY OF THE INVENTION

It is accordingly the object of the present invention to provide grasping or gripping forceps which provides an effective stopper function in a direction in which a movable operation handle is opened and closed and can provide this function without a bar to performing a gripping operation and can adjustably vary the stopper position.

In order to achieve the aforementioned object grasping or gripping forceps is provided which comprises:

a sheath having openable/closable gripping sections at its distal end;

a fixed operation handle provided on a proximal end portion of the seath;

a movable operation handle rotatably connected to the fixed operation handle;

an operation shaft having one end connected to a rotation operation end of the movable operation handle and the other end portion inserted through the fixed operation handle and sheath so as to be movable back and forth, the other end side being connected to the distal gripping sections and the operation shaft enabling the distal gripping sections to be opened and closed through the forward and backward movements by the rotation operation of the movable operation handle;

a first stopper provided at an area of the fixed operation handle, through which the operation shaft is inserted, and restricting an end-of-forward movement of the operation shaft; and a second stopper provided at an area of the fixed operation handle, through which the operation shaft is inserted, and restricting an end-of-backward movement of the operation shaft, in which at least one of the first and second stoppers can adjustably vary the end-of-movement of the operation shaft.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention and, together with the general description given above and the detailed description of the preferred embodiments given below, serve to explain the principles of the invention.

FIG. 1 is a side view showing grasping or gripping forces (referred to hereafter as gripping forceps according to a first embodiment of the present invention;

FIG. 2 is a plan view, partly taken away, showing a gripping section of the forceps in FIG. 1;

FIG. 7 is a side view, partly taken away, showing a portion of a lock mechanism for restricting the rotation of a handle in the operation section of the forceps;

FIG. 8A is a side view generally showing gripping forceps according to a second embodiment of the present invention;

FIG. 8B is a plan view showing a forceps section of the gripping forceps of the second embodiment of the present invention;

FIG. 9 is a side view showing a forceps section of gripping forceps according to a third embodiment of the present invention;

FIG. 10 is a plan view showing a forceps section of gripping forceps according to a fourth embodiment of the present invention;

FIG. 11 is a transverse cross-sectional view showing a major portion of an operation section according to a fifth embodiment of the present invention;

FIG. 12 is a transverse cross-sectional view showing a major portion of an operation section of gripping forceps according to a sixth embodiment of the present invention;

FIG. 18A is a side view, partly taken away, showing a portion of a lock mechanism in a twelfth embodiment of the present invention;

FIG. 18B is an explanative view showing a forceps section in the gripping forceps according to the twelfth embodiment of the present invention;

DETAILED DESCRIPTION OF THE PREFERRED EMBODIMENTS

Figure 3:
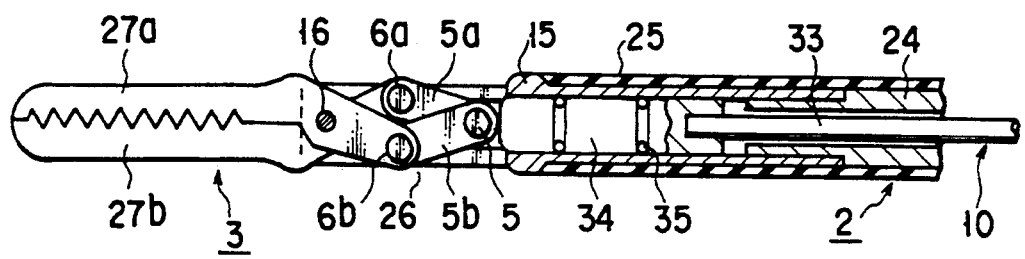
FIG. 3 is a side view, party taken away, showing the gripping section of the forceps in FIG. 1.

FIGS. 1 to 7 show a structure of gripping forceps according to a first embodiment of the present invention.

The gripping forceps 1 comprises an insertion section 2 inserted into a body cavity of a subject through a cannula of a cannula/trocar device, a forceps section (distal gripping section) 3 provided on the distal end of the insertion section 2 and an operation section 4 provided on the proximal end of the insertion section 2. The operation section 4 has a handle lock mechanism 8.

The insertion section 2 is formed of a tubular sheath 24 made of metal, such as stainless steel, and the outer surface of the sheath 24 is covered with an insulating tube 25 made of an insulating material, such as a fluorine-based resin. The sheath 24 has an insertion bore.

The forceps section 3 has a pair of gripping members 27a, 27b connected by a pin shaft 16 to a distal tip 15 which is provided on the distal end of the sheath 24. The pair of gripping members 27a, 27b can grip an organ in the body cavity of the subject, for example, the gallbladder, etc. The pair of gripping members 27a, 27b are of such a type that these members can be opened and closed by an operation shaft 10 as will be set out below through a link mechanism 26. As shown in FIGS. 2 and 3, the link mechanism 26 is so configured that a pair of links 5a, 5b are connected at their one end side to a coupling member 34, by a common pin 5, connected to the distal end of the operation shaft 10 and at their other end side, by a pair of pins 6a, 6b, to the corresponding end portions of the gripping members 27a and 27b.

The operation section 4 is remotely so operated as to open and close the gripping members 27a and 27b of the forceps section 3. The operation section 4 has a fixed operation handle 28 fixed to the base end of the sheath 24 and a movable operation handle 30 rotatably mounted by a setscrew pin 29 to the fixed operation handle 28.

Figure 6:
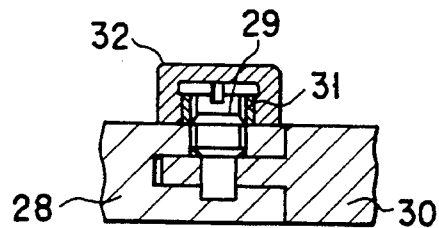
FIG. 6 is a cross-sectional view taken along line VI—VI in FIG. 1.

As shown in FIG. 6, a washer 31 is fitted over the setscrew pin 29 and a cap 32 is mounted on the head of the setscrew pin 29 by a bonding, a snap-fitting, etc., means and made of an electrically insulating material, such as rubber and plastics.

The forceps 1 has an operation shaft 10 for connecting the forceps section 3 to the operation section 4. The operation shaft 10 is inserted into the insertion bore of the sheath 24 such that it is movable back and forth. The distal end of the operation shaft is connected to the coupling member 34 as one integral unit. The operation shaft 10 is connected by the coupling member 34 to the link mechanism 26. O-rings 35 are fitted over the outer periphery of the coupling member 34. Each O-ring 35 is situated between the outer periphery surface of the coupling member 34 and the inner surface of the sheath 24 to keep the inside of the insertion section 2 airtight and watertight from the distal end side of the insertion section 2 of the forceps 1.

Figure 4:
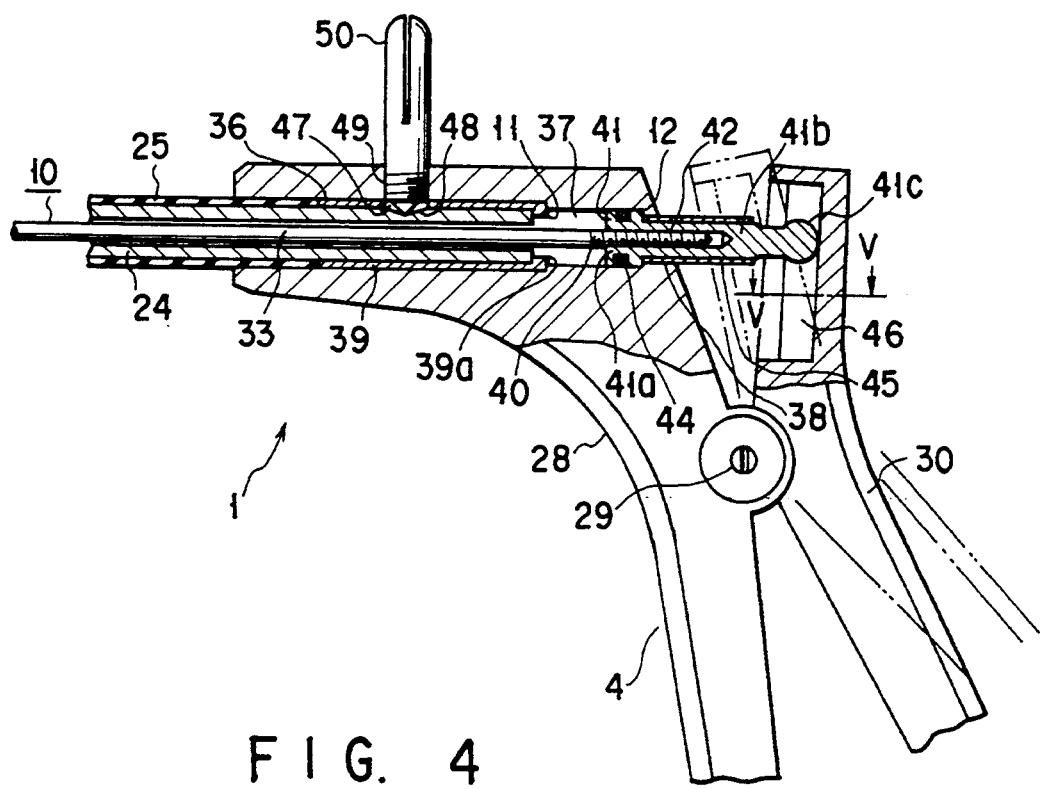
FIG. 4 is a transverse cross-sectional view showing an operation section of the forceps in FIG. 1.

As shown in FIG. 4, an enlarged view, an insertion section guide bore 36 is provided for inserting the sheath 24 from the forward end side of the handle 28 through the insulating tube 25. A rod holding bore 37 is connected to the insertion section guide hole 36 and has a diameter smaller than that of the guide hole 36. A through bore 38 is connected to the rod holding bore 37 and has a diameter smaller than that of the rod holding bore 37. These bores are formed in a straight line and extend through the upper portion of the fixed operation handle 28.

In the insertion section guide bore 36, an abutting pipe 39 is fitted relative to the end of the sheath 24 to prevent the electrically insulating tube 25 from slipping toward the operator's side. A rear end 39a of the abutting pipe 39 engages with the rear end face of the sheath 24 and has an inner wall surface smaller in diameter than the rod holding bore 37 with an inwardly extending flange-like area provided on the rear end 39a of the abutting pipe 39.

The operation shaft 10 has such a length that the proximal end portion of a shaft body 33 extends out of the end of the sheath 24 past the rod holding bore 37 and bore 38 and toward the outside via the fixed operation handle 28.

A coupling rod 41 is connected to the proximal end of the shaft body 33. An externally threaded portion 40 is provided on the outer periphery of the proximal end portion of the shaft body 33. The coupling rod 41 has an internally threaded portion 42 along its axis. By inserting the externally threaded portion 40 of the shaft body 33 into the internally threaded portion 42 of the coupling rod 41 the shaft body 33 is connected in a straight line to the coupling rod 41, thus providing an integral operation shaft 10.

Thus the shaft body 33 of the operation shaft 10 and coupling rod 41 are movable back and forth as one unit. By rotationally operating the coupling rod 41 relative to the shaft body 33 in a circumferential direction, both are axially displaced in a relative positional relation while maintaining the threaded relation of the externally and internally threaded portions 40 and 42 and the position of the coupling rod 41 relative to the shaft body 33 of the operation shaft 10 can be displaced along the axial direction of the coupling rod 41.

The coupling rod 41 has a large-diameter section 41a, a small-diameter section 41b and a bulb section 41c in a direction from the forward end toward the base end. The large-diameter section 41a is loosely fitted in the rod holding bore 37 and the small-diameter section 41b is loosely fitted in the through hole 38, with the coupling rod 41 advanced to the forward side the forward end face of the large-diameter section 41a of the coupling rod 41 abuts against the rear end 39a of the abutting pipe 39 so that both these two members provide a first stopper means 11 for restricting the end-of-forward movement of the operation shaft 10.

With the coupling 41 receded toward the rear side, a step defined between the large-diameter section 41a and the small-diameter section 41b is abutted against a step defined between the rod holding bore 37 and the through bore 38 so that these two steps provide a second stopper means 12 for restricting the end-of-backward movement of the operation shaft 10.

That is, the first stopper means 11 restricts the end-of-forward movement of the coupling rod 41 and the second stopper means 12 restricts the end-of-backward movement of the coupling rod 41. By rotationally operating the coupling rod 41 relative to the shaft body 33 of the operation shaft 10 in a peripheral direction a relative positional relation of both is shifted while maintaining the threaded relation of the externally and internally threaded portions 40 and 42. By axially displacing the coupling rod 41 back and forth relative to the operation shaft 10 it is possible to adjustably vary the position of each end of the backward and forward movements of the operation shaft 10. It is convenient to utilize a pair of pliers, etc., as a means for rotationally operating the coupling rod 41 in a peripheral direction.

An O-ring 44 is fitted over the portion of the outer periphery of the large-diameter section 41a of the coupling rod 41 such that the O-ring 44 is set in intimate contact with the inner wall surface of the rod holding hole 37. The small-diameter section 41b is rearwardly projected out of the rear end face of the fixed operation handle 28. The small-diameter section 41b of the coupling rod 41 is covered with a heat shrinkable tube 45 made of, for example, a fluorine resin material.

Figure 5:
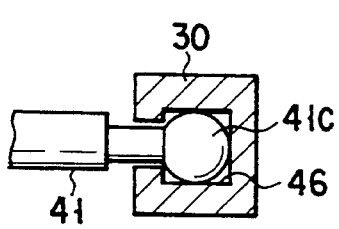
FIG. 5 is a cross-sectional view taken along line V—V in FIG. 4.

As shown in an enlarged view in FIG. 5, an elongated engaging groove 46 is formed, in an up/down direction, on that wall portion of the operation end portion of the movable operation handle which confronts the fixed operation handle 28. The bulb section 41c is fitted in the engaging groove 46 in an engaged relation. when the movable operation handle 30 is rotationally operated with the setscrew pin 29 as a fulcrum, the bulb section 41c is slidably moved in the engaging groove 46 in an engaged relation and displaced back and forth so that the operation shaft 10 is operated in a back/forth direction.

A through-hole 47 is provided at a given area in the outer peripheral wall of the abutting pipe 39. A hole 48 V-shaped in cross-section is provided at that outer peripheral wall area of the sheath 24 confronting the through-hole 47. In the area of the fixed operation handle 28 facing the through-hole 47 a screw hole 49 is provided where an electrode pin 50 is threadably inserted.

The electrode pin 50 has a conical end at its forward end and inserted through the through-hole 47 in the abutting pipe 39 into the hole 48 in the sheath 24 such that an engaged relation is achieved with the conical end down. The electrode pin 50 is adapted to be connected to a cord for transmitting a high-frequency current coming from a high-frequency power source not shown. The electrode pin is made of a metal material, such as stainless steel.

Further, the forceps 1 includes the handle lock mechanism 8 for locking the rotation movement of the movable operation handle 12 in a direction in which the handle 12 is opened. The lock mechanism 8 has a locking member 101 curved along a circular arc, as shown in FIG. 7, with the rotation center of the movable operation handle 30 as a fulcrum. One end of the locking member 101 is pivotally mounted, by a coupling pin 102, to the arm of the movable operation handle 30 partway of the arm. A section with continuous teeth 103 is provided on the inner surface side of the locking member 101. The rotation-end side of the locking member 101 forwardly extends through a slit-like hole 104 in the fixed operation handle 28. An operation lever section 105 is provided on the rotation forward end of the locking member 101. A ratchet pawl 106 is mounted on the fixed operation handle 28 at the slit-like hole (104) area and engages with the ratchet teeth 103 of the locking member 101. The ratchet pawl 106 is made up of a leaf spring and fixed by a setscrew 107 to the fixed operation handle 28.

A projection 108 is integrally mounted on the pivotal end of the locking member 101 and a leaf spring 109 is mounted on the fixed operation handle 28 by a setscrew 110 and pushed against the projection 108. The leaf spring 109 has its free end pushed against the projection 108 of the locking member 101 so as to urge the locking member 101 in a direction to rotate clockwise in FIG. 7. By the urging force of the leaf spring 109 the locking member 101 is urged in a direction to enable the ratchet pawl 106 to engage with the ratchet tooth 103. Stated in another way, the locking member 101 is normally urged to enable the ratchet pawl 106 to engage with the ratchet tooth 103. In this engaged state, the movable operation handle 30 is locked from being moved in a direction in which the handle 30 is opened.

The member of the ratchet pawl 106 is mounted by the setscrew 107 on the fixed operation handle 28 and, therefore, is detachable from the fixed operation handle 28 for replacement.

The operation of the forceps 1 thus arranged will be explained in detail below.

First, the movable operation handle 30 is opened and closed relative to the fixed operation handle 28 and, by so doing, the operation shaft 10 is moved forward and backward, thus opening and closing the gripping members 27a, 27b through the action of the link mechanism 26.

Stated in more detail, when the movable operation handle 30 is rotated about the setscrew pin 29 in a counterclockwise direction in FIG. 1, that is, in a direction in which the movable operation handle is opened relative to the fixed operation handle 28, then the operation shaft 10 is slidably moved forward and the gripping members 27a, 27b of the forceps section 3 are opened through the link mechanism 26. In this state, the forceps section 3 is located opposite a living tissue of interest of a subject.

When the movable operation handle 30 is rotated in a clockwise direction in FIG. 1, that is, in a direction in which the movable operation handle 30 is closed relative to the fixed operation handle 28, then the operation shaft 10 is slidably moved backward and the link mechanism 26 closes the gripping members 27a, 27b so that the living tissue of interest can be gripped.

When the gripping members 27a, 27b are closed so as to grip a given organ, such as the gallbladder, the ratchet pawl !06 is raised by the oblique back of the ratchet tooth 103 provided in the inner side portion of the locking member 101 so that the ratchet pawl passes over each ratchet tooth. When the rotation operation of the movable operation handle 30 is stopped, the ratchet pawl 106 engages with the corresponding ratchet tooth at that time under a rotational elastic urging force of the leaf spring 109 so that their locked state is achieved immediately. It is also possible to continue gripping the organ positively by the gripping members 27a, 27b. This locked state, being elastically urged in a direction to allow the gripping members 27a, 27b to be opened, still serves to maintain a firm engagement of the ratchet pawl 106 with the ratchet tooth 103.

It is to be noted that the ratchet pawl 106 can be disengaged from the locking member 101 when the operation lever section 105 on the .locking member 101 is pushed down against an urging force of the leaf spring 109.

When, as set out above, the movable operation handle 30 is to be operated, adjustment is made such that, when the gripping members 27a, 27b are placed in an ideal state of closure through the operation of the movable operation handle 30 so that no more than necessary force is exerted on the gripping members 27a and 27b, the coupling rod 41 of the operation shaft 10 is threadably moved relative to the shaft body 10 so that the coupling rod 41 abuts against the position corresponding to the second stopper means.

This restricts the second stopper means 12 to the rear end of the coupling rod 41, that is, the rear end of the operation shaft 10, even if the movable operation handle 30 is forced to be strongly and rotationally operated, during the closure of the gripping members 27a and 27b, to a more than necessary extent. It is thus possible to prevent an organ of interest from being injured and do so without exerting any excessive force upon the gripping members 27a and 27b and to prevent any damage to the forceps section 3.

When the movable operation handle 30 is rotationally operated away from the fixed operation handle, the coupling rod 41 is moved forward, finally reaching an action area of the first stopper means 11, that is, the end-of-forward movement of the coupling rod 41 is restricted and the opening angle of the gripping members 27a, 27b is thus restricted by the first stopper means. Even if during the opening of the gripping members 27a and 27b the movable operation handle 30 is rotationally operated with a more than necessary force, no such force is exerted on the forceps section, thus preventing any breakage to the forceps section. Further, the forceps section is not largely opened beyond a necessary extent.

In the present invention as set out above, since the ratchet pawl 106 of the lock mechanism 20 is mounted by a setscrew 107 on the fixed operation handle 10 and it is possible to remove the ratchet pawl 106 from the fixed operation handle 10. The ratchet pawl 106, being worn away, can readily be replaced by a new one. It is thus possible to improve the durability of the forceps through replacement of the ratchet pawl.

In the case where the amount of opening of the forceps section is to be adjusted, the coupling rod 41 of the operation shaft 10 is threadably moved relative to the shaft 33, thereby varying the position of the coupling rod 41. When, in this case, the coupling rod 41 is threadably advanced, the angle of opening of the gripping members 27a and 27b becomes smaller. When, on the other hand, the coupling rod 41 is threadably receded, that is, toward the operator side, it is possible to increase the angle of opening of the gripping members 27a, 27b. In this way, the gripping forceps 1 can be adjusted to an optimal angle of opening corresponding to a living tissue to be gripped.

The O-ring 44 is fitted over the large-diameter section 41a of the coupling rod 41 in a manner to be set in intimate contact with the inner wall surface of the rod holding bore 37. By so doing, the interior of the operation section 4 can be kept air-tight and watertight.

When the operation section 4 is operated, the small-diameter section 41b in particular of the coupling rod 41 is exposed from between the fixed operation handle 28 and the movable operation handle 30, but due to the heat-shrinkable tube 45 covering the exposed area no accident, such as a burn, occurs even if any "skin" contact takes place.

As shown in FIG. 6, when the setscrew pin 29 is to be mounted, it is threaded, by a minus-headed driver for instance, into the fixed operation handle 28 until the end face of the washer 31 is tightened. When this is achieved, the insulating cap 32 is fitted over the head of the setscrew pin 29.

Even if the setscrew pin 29 is very strongly fastened during the threadable insertion of the setscrew pin 29, as any insulating coating layer is not formed directly over the head of the set pin 29 no care needs to be exercised over a possible separation of the insulating coating layer. It is also possible to hold a positive insulating effect because the head of the pin is covered with the insulating cap 32.

Although in the first embodiment the small-diameter section 41b and bulb section 41c of the coupling rod 41 are provided as an integral unit, the present invention is not restricted thereto. The small-diameter section 41b and bulb section 41c can be made separate from each other in which case the small-diameter section 41b may be of such a type that it can be threadably inserted into the bulb section 41c.

In the first embodiment, although the insertion section 2 and forceps section 3 are arranged in a straight line, the present invention is not restricted thereto.

A second embodiment as shown in FIGS. 8A and 8B will now be explained below. An insertion section 2 of gripping forceps 1 comprises a large-diameter section 51 and small-diameter section 52.

As will be seen from FIG. 8A, the center axes Oa and Ob of the large-diameter insertion section 51 and small-diameter insertion section 52 align with each other in a side elevational view, but in a plane view as shown in FIG. 8B the large-diameter insertion section 51 and small-diameter insertion section 52 have their center axes Oa and Ob deviated from each other.

A forceps section 3 is provided on the distal end of the small-diameter insertion section 52. A pair of forceps members 53a, 53b constituting the forceps section 3 are arranged in a straight fashion relative to each other as shown in FIG. 8A and so operated as to be opened and closed in an up/down direction as in the case of the first embodiment.

In the plane view shown in FIG. 8B, the forceps members 53a, 53b are curvilinearly formed such that on the proximal end side connected to the small-diameter insertion section 52 the forceps members are made straight along the small-diameter insertion section 52, but that the forceps members are gradually curved toward their distal end. It is to be noted that a most forward tip of the distal end section of each member does not extend beyond a maximal outer-diameter line Oc.

In the case where the gripping forceps 1 is inserted into that cannula, not shown, of the trocar/cannula device which has an inner diameter equal to the outer diameter of the large-diameter insertion section 51, the distal end of the forceps members 53a, 53b can be smoothly inserted into the cannula because the distal end of these forceps members is bent in a range not exceeding the maximal outer line Oc of the large-diameter insertion section 51.

Since the distal end of the forceps members 53a, 53b is curved, when the living tissue is to be gripped by inserting these members into the body cavity, these members can readily gain access to a to-be-gripped site, such as the blood vessel or the back of the ureter.

FIG. 9 shows a third embodiment of the present invention which is so configured as to obtain the same advantages as those of the preceding embodiment. An insertion section 2 of gripping forceps 1 shown in FIG. 9 is so configured as set out above in connection with the preceding embodiment and no further explanation is omitted with the same numerals attached to those parts or elements corresponding to those shown in the preceding embodiments. In FIG. 9, a forceps section 3 is of such a type that a pair of forceps members 54a, 54b is curved from a straight base end with the distal end of these members made at an obtuse angle.

FIG. 10 shows a fourth embodiment of the present invention. In this embodiment, an insertion section 2 of gripping forceps 1 is so configured as set out in connection with the preceding embodiments and a forceps section 3 is of such a type that a pair of gripping members 55a, 55b have a somewhat large length of straight base end portion with a distal end portion of these members curved in a small radius of curvature.

In either case, the distal end portions of the forceps members 54a, 54b and 55a, 55b are so formed as not to exceed a maximal outer diameter line Oc of a large-diameter insertion section 51. As a result, the distal end portion of these members can readily be inserted through a cannula of a trocar/cannular device and these members can grip a living tissue, such as the blood and the back site of the ureter without being given any excessive force as set out in connection with the preceding embodiments.

FIG. 11 shows a major section of a fifth embodiment according to the present invention. The basic structure of this embodiment is the same as set out in connection with the preceding embodiment except in the following points. Stated in another way, the externally threaded portion 40 provided in the base end portion of the shaft body 33, as well as the associated internally threaded portion 42 provided in the coupled rod 41, is eliminated in the embodiment shown in FIG. 11. Instead, the proximal end portion of a shaft body 33 has three, axially extending through bores 61a, 61b and 61c provided at given intervals.

Further, a through hole 62 is provided in a small-diameter section 41b of a coupling rod 41 and has a pan-like end 62a. A pin 63 with a pan-like head 63a is inserted into the through bore 61b and one (for example, 61c) of the through bores 61a, 61b and 61c so that the shaft body 33 is coupled to the coupling rod 41.

The fifth embodiment has the same function as that of the first embodiment and is of such a type that, by inserting the pin 63 into any one of the through bores 61a, 61b and 61c, the coupling rod 41 can be axially adjusted in its connection position to the shaft body 33 and fixed there. As a result, the end-of-movement position of the first and second stopper means 11 and 12 can be adjusted in the axial direction of the operation shaft 10.

Although in the fifth embodiment the three through bores 61a, 61b and 61c are provided, any proper number of through holes may be selected depending upon an extent to which adjustment is made by the first and second stopper means 11 and 12.

FIG. 12 shows a major section of gripping forceps according to a sixth embodiment of the present invention. The sixth embodiment is substantially the same in its structure as set out in connection with the first embodiment except in the following points. That is, the externally threaded portion 40 provided in the proximal end portion of the shaft body 33, as well as the associated internally threaded portion 42 of the coupling rod 41, is eliminated from the sixth embodiment. Instead, a screw hole 65 is provided in the circumferential wall of a small-diameter section 41b of the coupling rod 41 and extends into an internal bore as shown in FIG. 12 and a setscrew 67 with a head 66 is threaded into the screw hole 65. By pushing the forward end of the setscrew 67 against the outer peripheral surface of the shaft body 33 it is possible to fix the coupling rod 41 to the shaft body 33 in any given insertion position.

This basic function is as set out above in connection with the associated preceding embodiment. By loosening the setscrew 67 it is possible to axially move the coupling rod 41 relative to the shaft body 33 and hence to movably adjust the end-of-movement position by first and second stopper means 11 and 12 in an axial direction of the operation shaft 10. Further the coupling rod 41 can be fixed to the shaft body 33 in a given position by tightening the setscrew 67 relative to the shaft body. According to the sixth embodiment, it is possible to select any proper tightening position by the setscrew 67 and to continuously select the end-of-movement position.

Figures 13A, 13B:
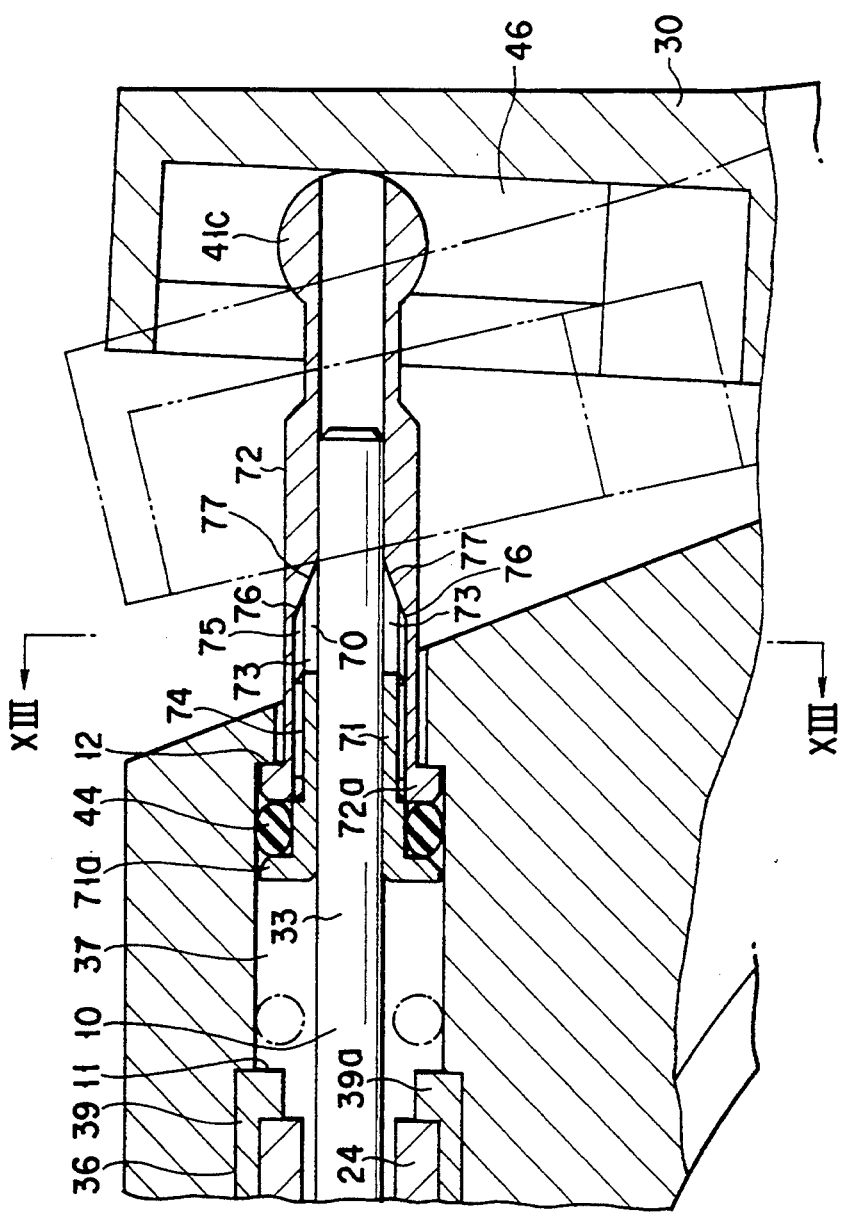
FIG. 13A is a transverse cross-sectional view showing a major portion of gripping forceps according to a seventh embodiment of the present invention.
FIG. 13B is a longitudinal cross-sectional view taken along line XIII—XIII in FIG. 13A.

FIGS. 13A and 13B show a major section of gripping forceps 1 according to a seventh embodiment of the present invention. This embodiment is substantially the same as in the first embodiment except in the following points. That is, the externally threaded portion 40 provided in a proximal end portion of the coupling body 33, as well as the associated internally threaded portion 42, is eliminated in the seventh embodiment. Instead, a coupling rod 41 has a mating bore, into which the proximal end portion of the shaft body 33 is inserted, and is comprised of two axially separated front- and back-side (first and second) coupling rods 71 and 72. An axially clamping chuck section 70 is provided on the front-side coupling rod 71 and has a plurality of slits 73 for clamping. Further, an externally threaded portion 74 is provided at the outer periphery of a middle portion of the first coupling rod 71.

An internally threaded portion 75 is provided in the inner bore of the front-side portion of the second coupling rod 72 and matingly threaded over the externally threaded portion 74 of the first coupling rod 71. The internally threaded portion 75 is so formed as to extend near the middle portion of the second coupling rod 72. A first slope (taper) portion 76 is provided near the terminal end portion of the internally threaded portion 75 and tapers toward the operator's side. The first slope portion 76 is provided in an opposed relation to a second slope (taper) portion 77 provided on the inner wall of the first coupling rod 71.

This basic function is the same as set out above. Here the externally threaded portion 74 of the first coupling rod 71 is threadably inserted into the internally threaded portion 75 of the second coupling rod 72 and the second coupling rod 72 is axially moved relative to the first coupling rod 71 so that the first slope 76 is abuttingly pushed against the second slope 77. By so doing, the slitted clamping chuck section 70 has its inner diameter contracted so that the first coupling rod 71 is tightened at the outer periphery of its middle portion. For this reason, the chuck section 70 is strongly set in tight contact with the outer periphery of a shaft body 33 whereby the first coupling rod 71 is fixed to the shaft body 33 and the second coupling rod 72 is fixed to the shaft body 33.

If the externally threaded portion 74 is reversely threaded away from the internally threaded portion 75 so as to move the second coupling rod 72 away from the first coupling rod 71 and toward the operator's side, then a push force on each slope portion (76, 77) is released so that an abutting engagement of the chuck portion 70 with the outer surface of the shaft body 33 is slackened to allow the first and second coupling rods 71 and 72 to be freely movable in the axial direction of the shaft body 33.

Flanges 71a and 72a serving as stoppers are provided on the front ends of the first and second coupling rods 71 and 72 and each have a diameter nearly the same as the inner diameter of a rod holding bore 37. An O-ring 44 is located between the flanges 71a and 72a.

By performing the aforementioned operation at a predetermined place on the proximal side of the shaft body 33, the positional relation of the first and second coupling rods 71 and 72 relative to the shaft body 33 can be adjusted in the axial direction of the operation shaft 10. It is also possible to adjust the distance between the flanges 71a and 72a. As a result, the end-of-movement position can arbitrarily and individually set by the first and second stopper means 11 and 12.

Figure 14:
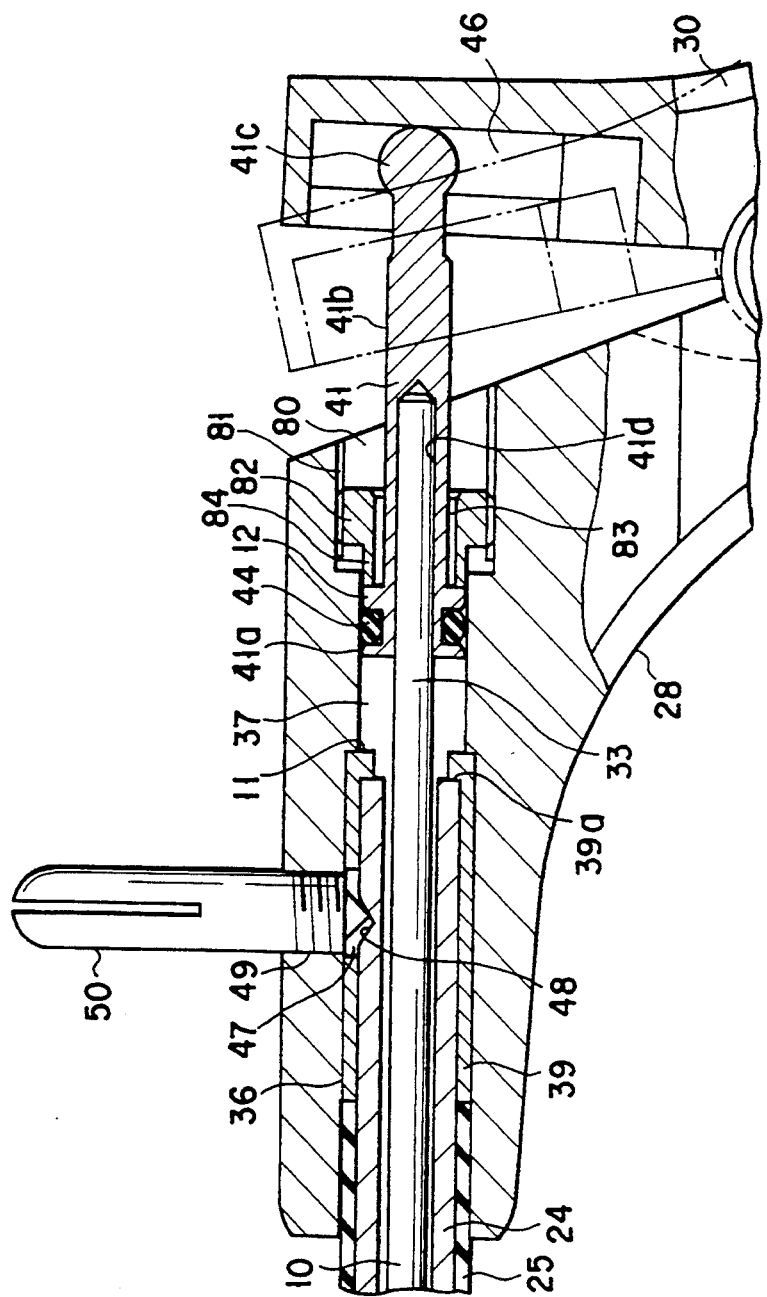
FIG. 14 is a transverse cross-sectional view showing a major portion of gripping forceps according to an eighth embodiment of the present invention.

FIG. 14 shows a major section of gripping forceps 1 according to an eighth embodiment of the present invention. The eighth embodiment is substantially the same in structure to the first embodiment except in the following points. That is, a bore 41d is provided on the forward end side section of the coupling rod 41 and a proximal-side end portion of a shaft body 33 is inserted in the bore 41a and fixed there by a fixing means, such as brazing or bonding.

Further, instead of the through bore 38 of the fixed operation handle 28 a bore 80 is provided from the proximal end side and an internally threaded portion 81 is formed in the bore 80. A screw member 82 is threaded into the bore 80. A bore 83 which is greater in diameter than a small-diameter section 41b is provided in the screw member 82 to allow the small-diameter section 41b of the coupling rod 41 to pass through. A cylindrical stopper 84 is provided in the forward end portion of the screw member 82 and has such an outer diameter as to be held in a rod holding bore 37 of the fixed operation handle 28.

When the coupling rod 41 is moved backward, a boundary step between the large-diameter section 41a and the small-diameter section 41b of the coupling rod 41 abuts against the forward end of the stopper section 84 of the screw member 82. By so doing the second stopper means 12 is provided. The screw member 82 can be axially moved by threadably moving the screw member 82 relative to the internally threaded portion 81 of the fixed operation handle 28. By so doing it is possible to continuously and arbitrarily adjust the end-of-movement position by the second stopper means 12.

Figure 15:
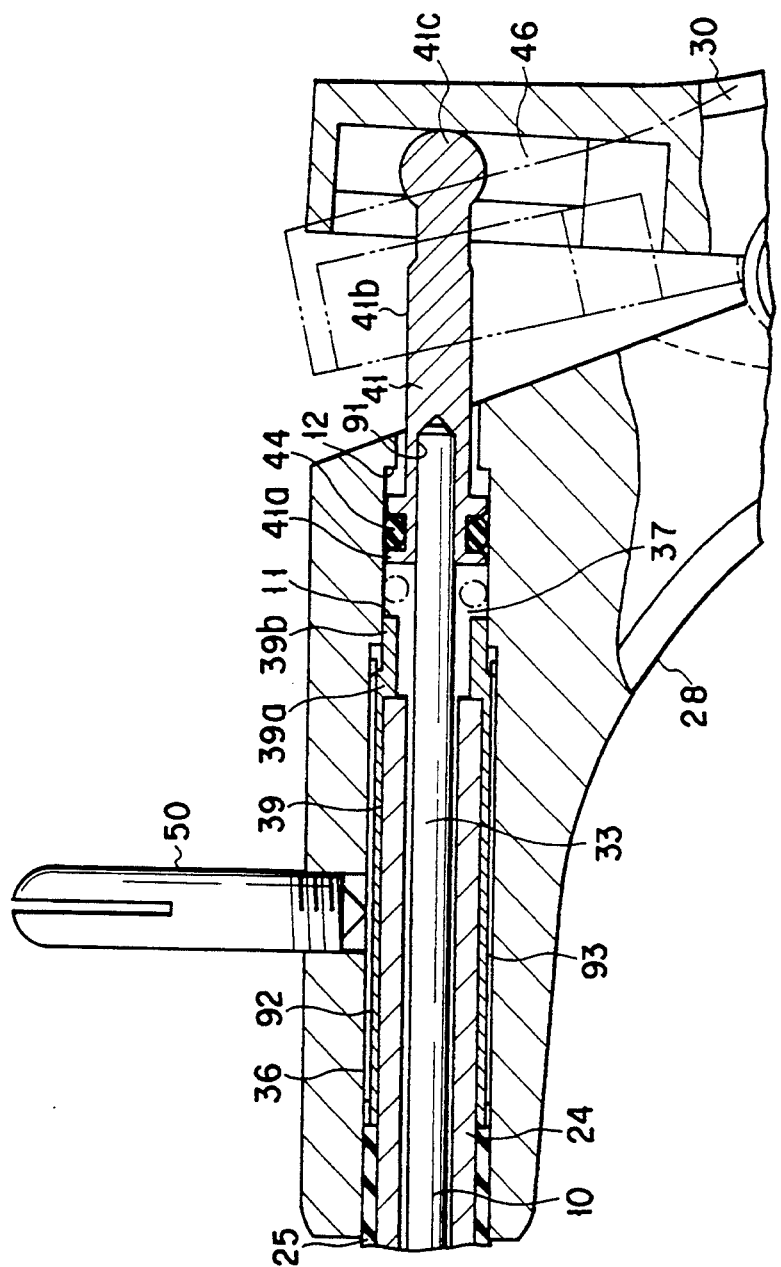
FIG. 15 is a transverse cross-sectional view showing a major portion of gripping forceps according to a ninth embodiment of the present invention.

FIG. 15 shows a section of gripping forceps 1 according to a ninth embodiment of the present invention. This embodiment is substantially the same in structure as the first embodiment except in the following points. That is, a hole 91 is coaxially provided in the forward end portion of a coupling rod 41 and opened at the forward end side. The proximal-end side portion of the shaft body 33 is inserted in the open forward end of the coupling rod 41 and fixed there by a fixing means such as brazing or bonding.

An internally threaded portion 92 is provided in the portion of an insertion section guide bore 36 of a fixed operation handle 28 and an externally threaded portion 93 is provided on the outer periphery of an abutting pipe 39. The abutting pipe 39 is threaded in the insertion section guide bore 36. The rear end portion of the abutting pipe 39 extends toward the proximal side and a stopper section 39b is provided at that rear end and has such an external diameter as to be held in a rod holding bore 37 of the fixed operation handle 28.

With the forward end of the coupling rod 41 in an advanced state the end face of a large-diameter section 41a abuts against the stopper section 39b of the abutting pipe 39, thus providing a first stopper means 11.

This basic function is as set out above in connection with the preceding embodiment. By threadably inserting the abutting pipe 39 into the internally threaded portion 92 of the fixed operation handle 28 the abutting pipe 39, sheath 24 and insulating tube 25, together with an operation shaft 10, are moved as one unit. This arrangement can adjust the end-of-movement position of a second stopper means 12 through a back/forth movement. At that time, the first stopper means 11 remains unchanged.

Figure 16:
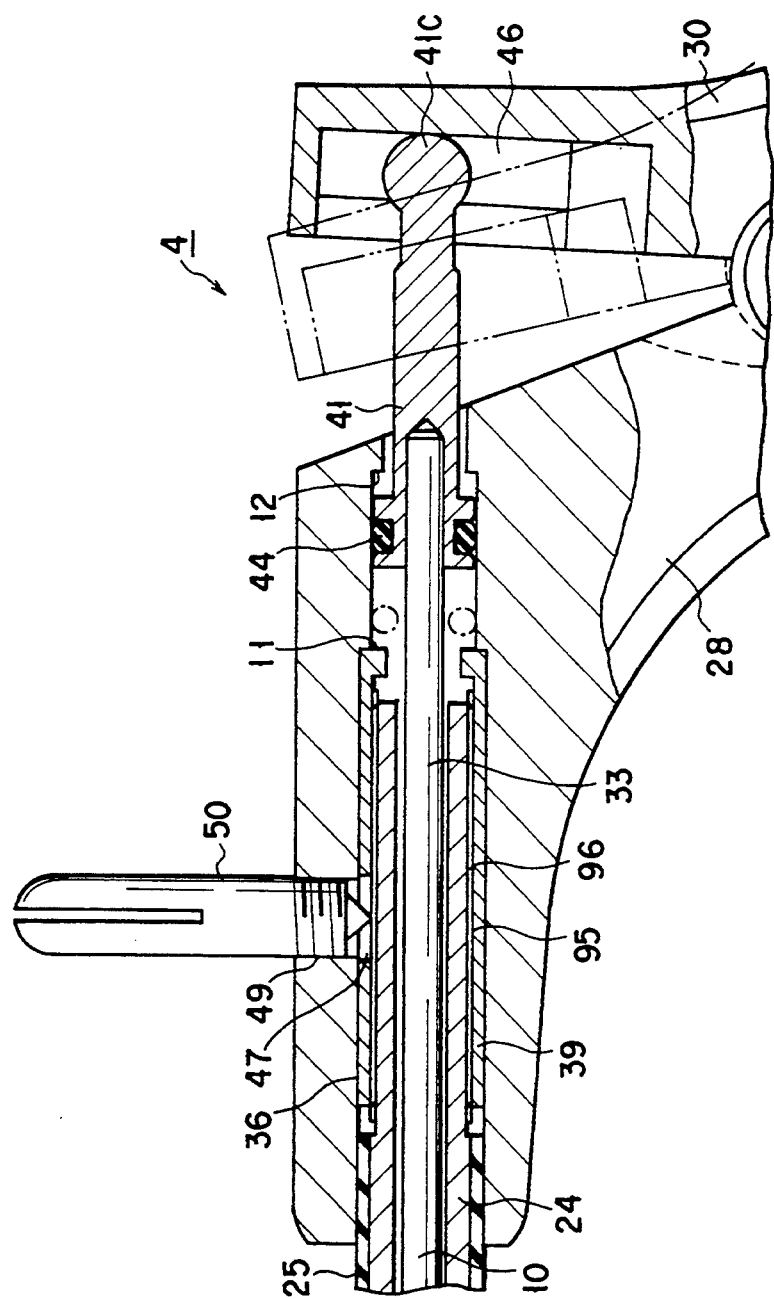
FIG. 16 is a transverse cross-sectional view showing a major portion of gripping forceps according to a tenth embodiment of the present invention.

FIG. 16 shows the arrangement of a major section of gripping forceps 1 according to a tenth embodiment of the present invention. This embodiment is substantially the same in arrangement as the preceding embodiment, but in this embodiment a connection structure of a shaft body 33 and coupling rod 41 constituting an operation shaft 10 is the same as in the eighth and ninth embodiments.

An internally threaded portion 95 is provided in the inner wall of an abutting pipe 39 and an externally threaded portion 96 is provided in that outer peripheral portion of a sheath 24 at an area near its operator-side end. The abutting pipe 39 is connected to the sheath 24 by threadably inserting the externally threaded portion of the latter into the internally threaded portion of the former.

This basic function is the same as set out above. The sheath 24 and insulating tube 25 and the operation shaft 10 are moved in a back/forth direction relative to the abutting pipe 39 and fixed operation handle 28 by threadably inserting the sheath 24 relative to the abutting pipe 39. It is possible, therefore, to simultaneously adjust the end-of-movement position in a back/forth direction by the first and second stopper means 11 and 12.

It may be possible to properly combine the adjusting means of the first and second stopper means 11 and 12 as set out above.

As set out above, the coupling rod is threadably coupled to the operation shaft for operating the forceps and insertably set to the fixed operation handle which, together with the movable operation handle, constitutes the operation section. The first and second stopper means for restricting an end-of-forward movement and end-of-backward movement position are provided at the fixed operation handle and coupling rod whereby the respective stopper means offer no bar to the gripping operation of the forceps. Further an effective stopper function can be achieved when the movable operation handle is opened and closed. It is possible to adjust the end-of-movement position by the stopper means.

Figure 17:
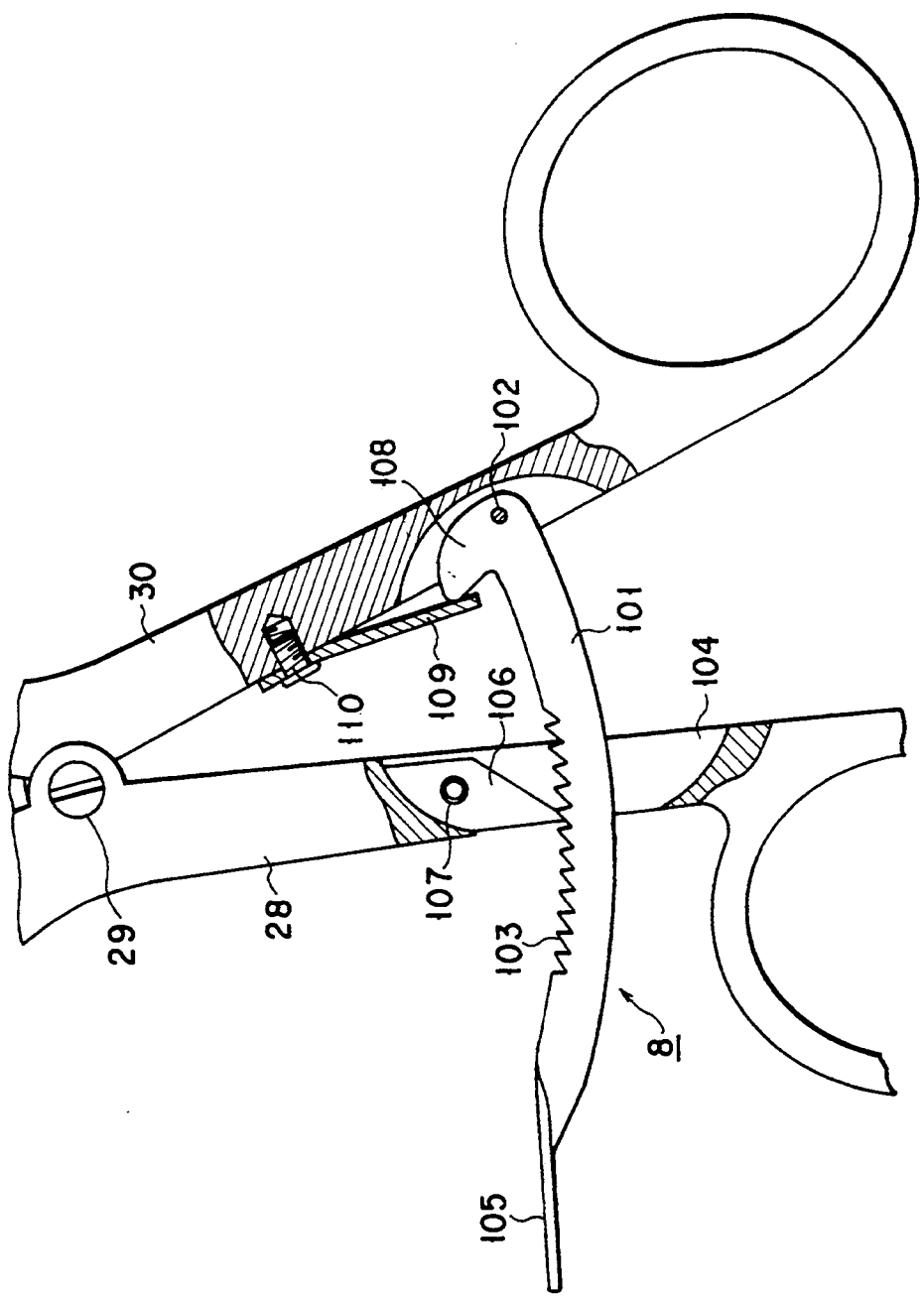
FIG. 17 is a side view, partly taken away, showing a lock mechanism in griping forceps according to an eleventh embodiment of the present invention.

FIG. 17 shows a variant of the aforementioned handle lock mechanism 8. In the variant, a member of a ratchet pawl 106 engaging with a ratchet teeth 103 of a locking member 101 is located in a slit-like hole 104 of a fixed operation handle 28 and fixed there by a setscrew 107. The member of the ratchet pawl 106 is made up of a plate member, The plate member has its surface located along the rotational direction of a movable operation handle 30.

In this arrangement, the shape of the member of the ratchet pawl 106 can be thickened in a direction in which a force acts and added strength can be imparted to the member. The side face of the member is pushed by the side face of the slit-like hole 104 and hence the member is hard to deform.

The ratchet teeth 103 of the locking member 101 need not be made constant in their pitch and, as shown in FIGS. 18A and 18B, may be arranged in a step-like decreased pitch $a_1 > b_1 > c_1$ in a manner to have pitches $a_1$, $b_1$ and $c_1$ correspond to respective ranges a, b and c. In this arrangement, at a start phase of closing operation, the gripping members 27a, 27b are fast closed because the corresponding pitch portion of the ratchet teeth is greater, but at a near-end phase of gripping an organ of interest it is possible to grip a varying size of organs in a delicate closing operation because the corresponding pitch portion of the ratchet teeth is smaller.

Figure 19A:
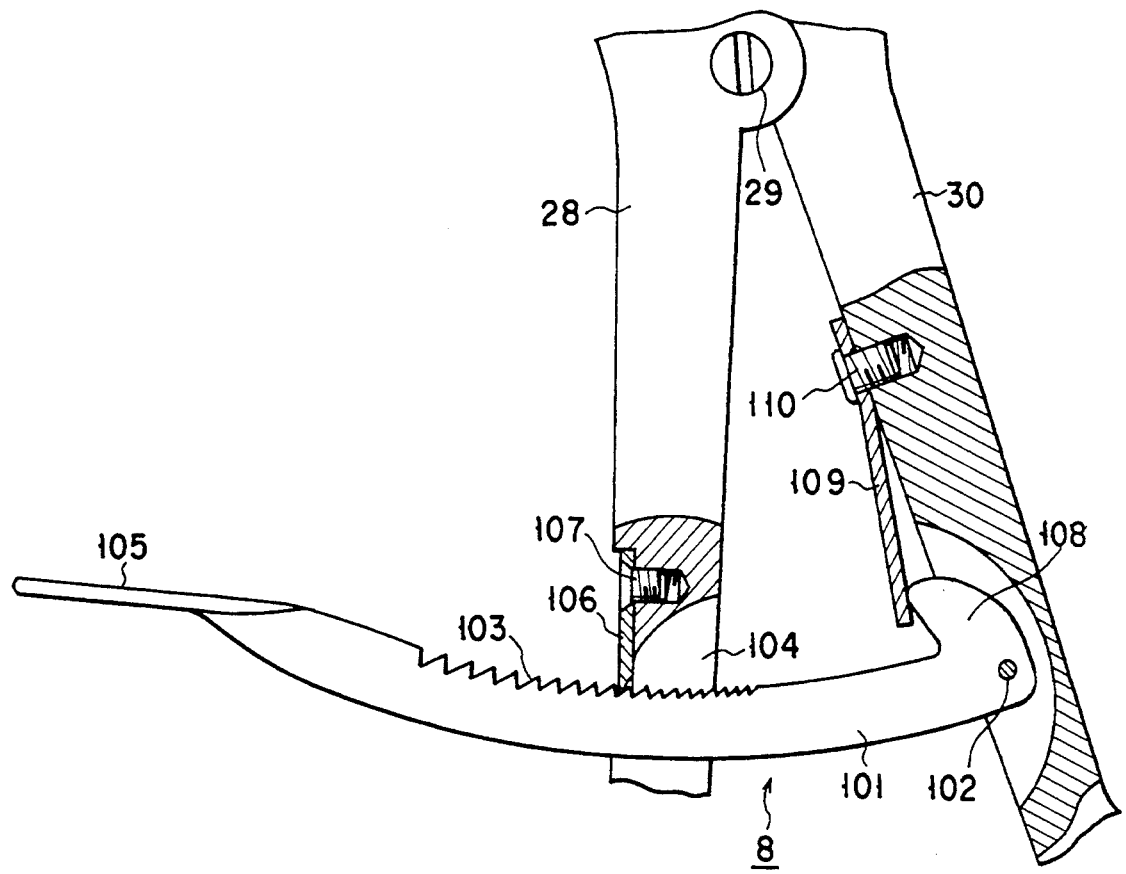
FIG. 19A is a side view, partly taken away, showing a portion of a lock mechanism in gripping forceps according to a thirteenth embodiment of the present invention.
Figure 19B:
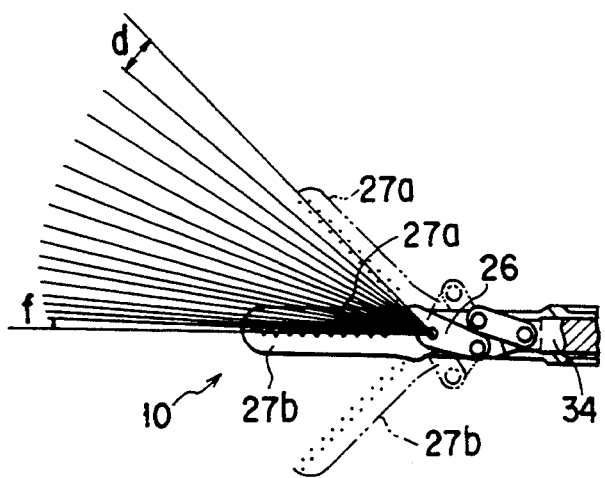
FIG. 19B is an explanatory view showing a forceps section in gripping forceps according to the thirteenth embodiment of the present invention.

In FIGS. 19A and 19B, the pitch of the ratchet teeth 103 may be so varied as to be gradually decreased from a range d to a range f. In this variant, it is possible to obtain the same effect as in the preceding embodiment.

Although in the first embodiment the locking member 101 is mounted on the movable operation handle 30, it may be possible to mount the locking member 101 and leaf spring 109 on the fixed operation handle 28 side and the ratchet pawl 106 on the movable operation handle 30 side. Since the member of the ratchet pawl 106 of the locking member 101 can be detachably mounted on either one of the fixed operation handle 28 and movable operation handle 30, it can readily be replaced by a new one even in the case where the ratchet pawl 106 is worn out. It is, therefore, possible to improve the durability of the gripping forceps.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. Grasping forceps for medical treatment which grips an object of interest in a body cavity of a subject, comprising:
   a sheath to be inserted into the body cavity and having an insertion bore therein;
   openable/closable gripping means provided on a distal end of the sheath, for gripping the object of interest in the body cavity, the gripping means being provided with an operation action end portion;
   a fixed operation handle provided at a proximal end portion of the sheath, said fixed operation handle having a bore therein;
   a movable operation handle rotatably coupled to the fixed operation handle and having an operation action end portion;
   an operation shaft inserted through the insertion bore and the bore of said fixed operation handle so as to be movable back and forth, the operation shaft having a distal end connected to the gripping means and a proximal end portion connected to the operation action end portion of the movable operation handle to allow the operation shaft to be moved back and forth by the rotation of the movable operation handle to close and open the gripping means;
   first stopper means for restricting an end-of-forward movement position of the operation shaft;
   second stopper means for restricting an end-of-backward movement position of the operation shaft;
   at least one of said first and second stopper means is received in said bore of said fixed operation handle; and means for adjustably varying an end-of-movement position of the operation shaft through at least one of the first and second stopper means; and
   wherein the operation shaft includes a rod portion having an enlarged section at a rear end of the rod portion, and the operation action end portion of the movable operation handle has a groove in which the enlarged section of the rod portion is set in fitting engagement.

2. Grasping forceps for medical treatment which grips an object of interest in a body cavity of a subject, comprising:
   a sheath to be inserted into the body cavity and having an insertion bore therein;
   openable/closable gripping means provided on a distal end of the sheath, for gripping the object of interest in the body cavity, the gripping means being provided with an operation action end portion;
a fixed operation handle provided at a proximal end portion of the sheath, said fixed operation handle having a bore therein;
a movable operation handle rotatably coupled to the fixed operation handle and having an operation action end portion;
an operation shaft inserted through the insertion bore and the bore of said fixed operation handle so as to be movable back and forth, the operation shaft having a distal end connected to the gripping means and a proximal end portion connected to the operation action end portion of the movable operation handle to allow the operation shaft to be moved back and forth by the rotation of the movable operation handle to close and open the gripping means;
first stopper means for restricting an end-of-forward movement position of the operation shaft;
second stopper means for restricting an end-of-backward movement position of the operation shaft;
at least one of said first and second stopper means is received in said bore of said fixed operation handle; and
means for adjustably varying an end-of-movement position of the operation shaft through at least one of the first and second stopper means;
wherein the operation shaft has an abutting end, and the first stopper means has an end face against which the abutting end abuts in the end-of-forward movement position of the operation shaft; and
wherein the fixed operation handle has a bore through which the operation shaft is inserted, and the first stopper means has a cylindrical member fitted into the bore of the fixed operation handle, said cylindrical member having said end face.

3. The forceps according to claim 2, wherein the cylindrical member has means for varying a position of said first end face.

4. The forceps according to claim 2, wherein the cylindrical member has means, threaded into said bore of the fixed operation handle, for varying a position of said first end face.

5. Grasping forceps for medical treatment which grips an object of interest in a body cavity of a subject, comprising:
a sheath to be inserted into the body cavity and having an insertion bore therein;
openable/closable gripping means provided on a distal end of the sheath, for gripping the object of interest in the body cavity, the gripping means being provided with an operation action end portion;
a fixed operation handle provided at a proximal end portion of the sheath, said fixed operation handle having a bore therein;
a movable operation handle rotatably coupled to the fixed operation handle and having an operation action end portion;
an operation shaft inserted through the insertion bore and the bore of said fixed operation handle so as to be movable back and forth, the operation shaft having a distal end connected to the gripping means and a proximal end portion connected to the operation action end portion of the movable operation handle to allow the operation shaft to be moved back and forth by the rotation of the movable operation handle to close and open the gripping means;
first stopper means for restricting an end-of-forward movement position of the operation shaft;
second stopper means for restricting an end-of-backward movement position of the operation shaft;
at least one of said first and second stopper means is received in said bore of said fixed operation handle; and
means for adjustably varying an end-of-movement position of the operation shaft through at least one of the first and second stopper means;
wherein the operation shaft has an abutting end, and the second stopper means has an end face against which the abutting end abuts in the end-of-forward movement position of the operation shaft; and
wherein the fixed operation handle has a bore through which the operation shaft is inserted and a member threaded into the bore, and said end face is provided on said member and has its position varied in accordance with an extend to which the member is threaded into the bore.

6. The forceps according to claim 5, wherein:
the fixed operation handle has a bore through which the operation shaft is inserted; and
said end face is formed by a step provided in an inner surface of the bore.

7. Grasping forceps for medical treatment which grips an object of interest in a body cavity of a subject, comprising:
a sheath to be inserted into the body cavity and having an insertion bore therein;
openable/closable gripping means provided on a distal end of the sheath, for gripping the object of interest in the body cavity, the gripping means being provided with an operation action end portion;
a fixed operation handle provided at a proximal end portion of the sheath, said fixed operation handle having a bore therein;
a movable operation handle rotatably coupled to the fixed operation handle and having an operation action end portion;
an operation shaft inserted through the insertion bore and the bore of said fixed operation handle so as to be movable back and forth, the operation shaft having a distal end connected to the gripping means and a proximal end portion connected to the operation action end portion of the movable operation handle to allow the operation shaft to be moved back and forth by the rotation of the movable operation handle to close and open the gripping means;
first stopper means for restricting an end-of-forward movement position of the operation shaft;
second stopper means for restricting an end-of-backward movement position of the operation shaft;
at least one of said first and second stopper means is received in said bore of said fixed operation handle;
means for adjustably varying an end-of-movement position of the operation shaft through at least one of the first and second stopper means;
wherein the operation shaft has a shaft body and a rod attached to a rear end of the operation body and is connected to the operation action end portion of the movable operation handle via the rod; and
adjusting means for adjustably varying a connection position of the rod to the shaft body and wherein the rod has a first abutting end for abutting against the first stopper means in an end-of-forward movement position of the operation shaft and a second abutting end for abutting against the second stopping means.

8. The forceps according to claim 7, wherein the adjusting means comprises:

a first hole formed in one of the shaft body and rod;

a plurality of second holes provided in the other of the shaft body and rod, and provided in a spaced-apart relation to an axial direction of the operation shaft; and a connection pin inserted into both a selected on of the second holes and the first hole.

9. The forceps according to claim 7, wherein a mutually fitted shaft body and rod are provided such that a connection pin is threaded in one of the shaft body and rod and is abutted in the other.

10. The forceps according to claim 7, wherein:

the rod has a bore into which a proximal end portion of the shaft body is fitted; and the adjusting means has a chuck for holding the rod therearound.

11. Grasping forceps for medical treatment which grips an object of interest in a body cavity of a subject, comprising:

a sheath to be inserted into the body cavity and having an insertion bore therein;

openable/closable gripping means provided on a distal end of the sheath, for gripping the object of interest in the body cavity, the gripping means being provided with an operation action end portion;

a fixed operation handle provided at a proximal end portion of the sheath, said fixed operation handle having a bore therein;

a movable operation handle rotatably coupled to the fixed operation handle and having an operation action end portion;

an operation shaft inserted through the insertion bore and the bore of said fixed operation handle so as to be movable back and forth, the operation shaft having a distal end connected to the gripping means and a proximal end portion connected to the operation action end portion of the movable operation handle to allow the operation shaft to be moved back and forth by the rotation of the movable operation handle to close and open the gripping means;

first stopper means for restricting an end-of-forward movement position of the operation shaft;

second stopper means for restricting an end-of-backward movement position of the operation shaft;

at least one of said first and second stopper means is received in said bore of said fixed operation handle; and means for adjustably varying an end-of-movement position of the operation shaft through at least one of the first and second stopper means;

wherein the operation shaft has an abutting end, and the second stopper means has an end face against which the abutting end abuts in the end-of-forward movement position of the operation shaft; and wherein the second stopper means comprises varying means for varying a position of the second end face for determining and end-of-movement position of the operation shaft.

12. The forceps according to claim 11, wherein the varying means comprises:

a member with an end face against which the operation shaft abuts at its end-of-movement position; and means for threadably inserting the member into the fixed operation handle.

* * * * *